United States Patent [19]
Seidah et al.

[11] Patent Number: 5,840,529
[45] Date of Patent: Nov. 24, 1998

[54] MAMMALIAN PRO-HORMONE CONVERTASE

[75] Inventors: Nabil G. Seidah, Iles-des-Soeurs; Robert Day, Ste-Dorothée; Michel Chrétien, Montreal, all of Canada

[73] Assignee: Clinical Research Institute of Montreal, Montreal, Canada

[21] Appl. No.: 545,562

[22] Filed: Oct. 19, 1995

Related U.S. Application Data

[63] Continuation-in-part of Ser. No. 517,015, Aug. 18, 1995, abandoned, and Ser. No. 510,347, Aug. 2, 1995, abandoned.

[51] Int. Cl.$^6$ .......................... C12P 21/00; C12N 15/63; C07H 21/04; C07K 14/00
[52] U.S. Cl. .................... 435/69.1; 435/320.1; 435/325; 530/326; 530/328; 530/350; 536/23.2
[58] Field of Search ................................. 435/69.1, 70.1, 435/172.3, 320.1; 530/350, 326, 328; 536/23.2, 23.5; 935/23, 24, 27, 66, 70, 72

[56] References Cited

PUBLICATIONS

Decroly, E., et al., (1994). *Journal of Biological Chemistry.* 269(16):12240–12247.
Gillespie, M. T., et al. (1995). *J. Cell. Biochem. Suppl.* 19B, p. 243, Abstract No. B7—102.
Johnson, R. C., et al. (1994) *Endocrinology.* 135:1178–1185.
Ohnishi, Y., et al. (1994). *Journal of Virology.* 68(6):4075–4079.
Seidah, N. G., et al. (1994). *Biochimie.* 76:197–209.
Seizen, R. J., et al. (1994). *Eur. J. Biochem.* 222:255–266.
Takahashi, S., et al. (1993). *Biochem. Biophys. Res. Commun.* 195(2):1019–1026.
Tsuji, A. S. (1994). *Biochem. Biophys. Res. Commun.* 202:1452–1459.

*Primary Examiner*—George C. Elliott
*Assistant Examiner*—Robert Schwartzman
*Attorney, Agent, or Firm*—Quarles & Brady

[57] ABSTRACT

This invention relates to a novel and seventh member of the subtilisin-kexin family isolated from rat, which has been named rPC7. The rat spleen cDNA has been totally sequenced. A shorter DNA sequence has been obtained for human, which corresponds to a portion of the catalytic region of a human pro-hormone convertase corresponding to the rat pro-hormone convertase. PC7 clearly distinguishes from the other mammalian members of the subtilisin-kexin family. Its tissue distribution is ubiquitous, but its presence is particularly remarkable in lymphoid tissues. It is present in LoVo cells that are able to cleave the HIV gp160 protein into active gp120/gp41 proteins and that are deficient in other effective pro-hormone convertases known up to date. Therefore, it is proposed that PC7 is a good candidate as a maturation enzyme responsible for the conversion of HIV gp160 protein in target $CD^{+4}$ cells.

22 Claims, 7 Drawing Sheets

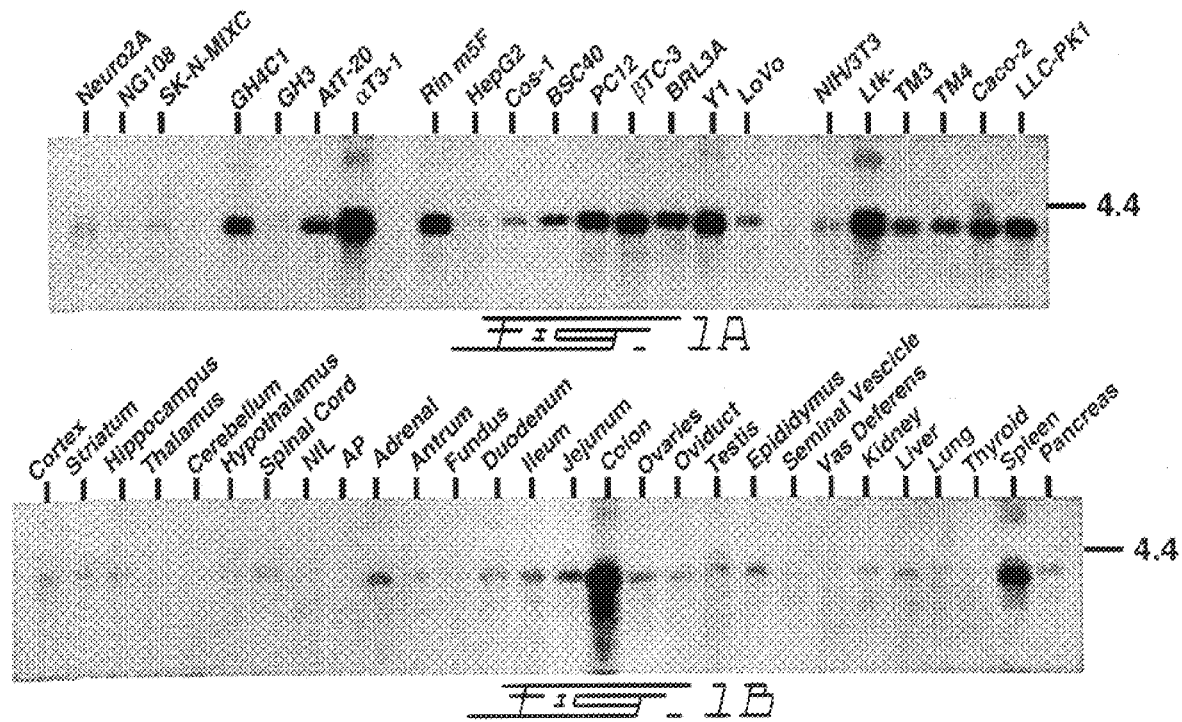

```
270
AlaLeuGlnHisGlyValMetAlaGlyPheGlySerIlePheValValAlaSerGlyAsnGlyGlyGlnHisAsnAsp
GCCTTACAACATGGAGTGATGGCTGGTTTTGAAGTATCTTTTGGTTGCCCAGTGGTAATGGTGGCCAGCACAATGAC 1219
        280                        290 ◆◆
                                       300
AsnCysAsnTyrAspGlyTyrAlaAsnSerIleTyrThrValThrIleGlyAlaValAspGluGlyLeuArgMetProPheTyrAla
AACTGCAACTATGATGGCTATGCCAACTCCATCTACACTGTCACCATAGGAGCTGTGGATGAGGGACGAATGCCTTTTATGCA 1306
              310                        320                       330
                                                                 350
GluGluCysAlaSerMetLeuAlaValThrPheSerGlyGlyAspLysMetLeuArgSerIleValThrThrAspTrpAspLeuGln
GAGGAGTGCGCCTCCATGCTGGCAGTCACCTTCAGTGGAGACAAGATGCTGCGGAGCATTGTGACTACTGACTGGGACCTTCAG 1393
         360◆                                      380
                                ◆◆370
LysGlyThrGlyHisGluGlyHisThrGlyThrSerAlaAlaAlaAlaProLeuAlaAlaAlaGlyMetIleAlaLeuMetLeuGlnVal
AAGGGCACTGGCTGCACTGGAAGGCCACACAGGAACCTCAGCTGCAGCCCCTCTAGCTGCAGCTGGCATGATAGCTCTCATGCTGCAGGTG 1480
             390                                    410
                                 400
ArgProCysLeuThrTrpArgAspValGlnHisIleIleValPheThrAlaThrGlnTyrGluAspHisArgAlaAspTrpLeuThr
CGGCCCTGCCTCACGTGGCGGGATGTCCAGCACATCATTGTCTTCACAGCCACTCAGTATGAAGATCATCGTGCAGACTGGCTCACT 1567
          420                        440
                      430
AsnGluAlaGlyPheSerHisSerHisGlnHisGlyPheLeuLeuAsnAlaTrpArgLeuValAsnAlaAlaLysIleTrpThr
AATGAGGCTGGATTCAGCCACAGCCATCAGCATGGTTTCGCCTGCTCAACGCCTGAGACTTGTCAATGCAGCCAAGATCTGGACG 1654
                                                  470
                 450                       460
SerValProTyrLeuAlaSerTyrValSerProMetLeuLysProArgSerProHisSerLeuGluValLeu
TCTGTCCCTTACTTAGCTTCCTATGTCAGCCCCATGCTGAAAGAAATAAGGCTGTTCCACGTTCCCCCCACTCTCTGGAGTCCTA 1741
◆◆◆              480                       500
                                           490
TrpAsnSerArgThrAspLeuGluMetSerGlyLeuArgAspValHisValAlaAlaValThrValSerIleThrHisProArg
TGGAATGTCAGACGGACCTGGAGATGTCGGGCTGCGGGACGTGCACGTTGCTGCAGTTCTCCATCACTCACCACGA 1828
✶ ✶                                                 530
              510                       520
ArgGlySerLeuGluLeuLysLeuPheCysProSerGlyMetMetSerLeuIleGlyAlaProArgSerAspSerProAsn
CGTGGCAGCTTAGAACTGAAACTGTTTTGTCCCAGTGGCATGATGTCTTTGATCGGCGCCCGCAGCGACTCGGACCCTAAC 1915
              540                       550
GlyPheAsnAspTrpThrPheSerThrValArgCysTrpGlyValGluArgAlaArgGlyValTyrArgLeuValIleArgAspValGly
GGCTTCAATGACTGGACATTTCCACTGTGCGGTGTGGGGAAAGAGCAAGAGAGTCTACAGACTGGTTATCAGGGATGTAGGA 2002
                                                              580
                        570
AspGluProLeuGlnValGlyIleLeuGlnTrpGlnLeuThrLeuTyrGlyLysSerThrTrpSerProValAspIleLysAspArg
GATGAGCCGCTCCAGGTGGGCATCCTCCAGTGGCAGCTGACGCTGTATGGCTCCAGTCCAGTAGACATCAAGGACAGA 2089
          590                        600 610
GlnSerLeuLeuGluSerAlaMetSerGlyLysTyrLeuHisAspPheThrLeuProCysProProGlyLeuLysIleProGlu
CAAAGTCTCTTAGAAAGTGCTATGAGTGGGAAATACCTGCATGACTTCACTCTGCCCTGCCCTCCACCTGGACTGAAAATTCCTGAG 2176
```

```
                                    630                              640
GluAspGlyTyrSerIleThrProAsnThrLeuLysThrLeuValLeuValGlyCysPheSerValPheTrpThrIleTyrTyrMet
GAGGATGGTTACAGCATTACCCCTAACACACTCAAGACCCTTGTGCTGGTTGGCTGCTTCAGTGTCTTCTGGACCATTACTACATG  2263
          650                     660                      670
LeuGluValCysLeuSerGlnArgSerThrHisGlyCysArgArgGlyCysCysProTrpProProGlnSerGlnAsn
CTAGAAGTGTGCCTGAGCCAGAGGAGCAAGGCTTCCACCATGGCTGCAGGAGAGGATGCTGCCCCCTGGCCCCCACAAAGCCAAAAC  2350
                                                                 700
SerLysGluValGlyThrAlaLeuGlyLeuSerMetProLeuCysSerSerLysAspLeuAspSerGluHisGlyAspCys
TCCAAGGAAGTGGGGACACTAGAATCAATGCCACTGTGCAGCAGCAAGGACCTGGATAGTGAGCACGGGGACTGC  2437
680**                                                     **        **730
          710                      720
ThrThrAlaSerSerLeuLeuAlaProGluLeuLeuGlyGluAlaAspTrpSerLeuSerLysAspLeuAspCys
ACAACTGCCTCTAGCTTGCTGGCCCCAGAGCTGCTGGGGGAAGCTGACTGGAGTCTGTCCCAGAACAGTAAGACCTGACCTGGATTGT  2524
                740                747
ProProHisGlnProProAspLeuLysAspGlyGlnIleCys
CCTCCCCACCAACCCCCAGACCTGAAGGATGGACAGATCTGCTGACCCCCAGAGCCCAGCTTCTTCCATGTACAACAGGCTCTTCCTA  2611
AACTTGGTTATGAGGCTTTCAATCATGATGCTCAGGAGAGAATGCTGCCACCAAGGCCTCCTCCTGACATCTGCACCCCTGAAGCATT  2698
CTCAGCCTTCTCAAGAGGGTGAGGGCCATCTTAATTAAGCGCAGTGGTTCATGCTCCTCTAGCTGTCCTGCCCAGCCCCTGAGCTTTGC  2785
TGAGAGCCTTTCGACAAGGGTTGGCGCCCAGG CCAGGCAGCAGGTGCCTGTATACCTAGGAACACTCTCAACAGAGCCGCGCCCATC  2872
AGGACCTCCACCCCCTTCACAAGTTATGCAAGACAGTTATGCAAGAGCCTTAGAAGCAGCAGGTGCCTTGTGCCCGTACCGAGGCCC  2959
AGAGAGGCTGGCAAGAGCTACACCCTTCCTGCTGCTGGGCTGGCGTGGCGTCTTCCTGTGTGCCTGTTCTGAAGCCCG  3046
TACCTTCACTACTACCACCACTGGGGAAGTGGCCTCAGGAAAACTGGAGGCACAGGATTCCAGCACCAGCACC  3133
CTTGCTGCCTGCCTCACTGGGCTGGCTGCCTGCCTGCAGAGAGCTGACTGCAGGGCCCTTCATCCAGAGGCCGTCCAGCTGTGTAATCCG  3220
ATGACCACCTGCTCTCCCCATCTTTTGCAAAGTGCTCTGCAGGAAATGCCTTCATTCCAGAGGCCCTGACTTTCCTCCATTCTT  3307
GGCCTTCTCCCCCTTCCCACCATCTTTGGAGCTAATTGTTAATATGAAATTTTGATTTACTTTTCAAAGCAACA  3394
TTTGTTGAATTTTTTCTGCACAGCTTTCCAAAATAAAAAAGCAGAAGT (AAAAAAAA)  3450
```

FIG. 3C

```
rPC7  917  GAAATTGCAGCTGTGCCCAACAACAGCTTCTGTGCAGTAGGTGTGGCCTA      966 hPC7    1  .................................TGCGCTGTGGGCGTAGCATA    20

967  TGGGAGCCGAATAGCAGGTATCCGGGTGCTGGATGGACCACTCACAGACA    1016
             |||||| || |||||||| ||||||||||||| ||||||||| ||||||
         21  TGGGAGCCGCATCGCAGGTATCCGGGTACTGGATGGACCTCTCACAGACA      70

1017  GTATGGAAGCTGTGGCATTCAACAAACACTATCAGATCAATGACATCTAC    1066
             | |||| || ||||| || |||| ||| | |||||||||||||||||||
         71  GCATGGAGGCGGTGGCGTTCAACAAGCACTACTCAGATCAATGACATCTAC     120

1067  AGCTGCAGCTGGGGGCCCCGATGATGATGGGAAGACAGTGGATGGTCCTCA    1116
             || |||||||||||| || ||||||||||||||||||| ||||| ||| |
        121  AGTTGCAGCTGGGGACCAGATGATGATGGGAGGACAGTGATGGCCCCCA      170

1117  TCAGCTTGGAAGGCTGCCCTTACAACATGGAGTGATGGCTGGTCGCCAAG    1166
             |||||||||||||||| ||||||||||| |||||| |||||||||||| |
        171  TCAGCTTGGAAAGGCTGCCCTTACAACATGGGGTGATTGCTGGTCGCCAGG     220

1167  GCTTTGGAAGTATCTTTGTGGTTGCCAGTGGTGGCCAGCACAAT    1216
             |||||||||| ||||| |||||||||||||| |||| |||| ||
        221  GCTTTGGGAGCATCTTTGTGGTAGCCAGTGGCAACGGTGGGGAGCATAAC     270

1217  GACAACTGCAACTATGATGGCTATGCCAACTCCATCTACACTGTCACCAT    1266
             |||||||| |||||| |||
        271  GACAACTGTAACTGT........................................    285
```

Fig. 4

```
rPC7  198  EIAAVPNNSFCAVGVAYGSRIAGIRVLDGPLITDSMEAVAFNKHYQINDIY  247
                    ||||||||||||||||||||||||||||||||||||||
hPC7    1  ..........CAVGVAYGSRIAGIRVLDGPLITDSMEAVAFNKHYQINDIY   40 rPC7  248  SCSWGPDDDGKTVDGPHQLGKAALQHGVMAGRQGFGSIFVVASGNGGQHN  297
           |||||||||| ||||||||||||||||| |||||||||||||||||: ||
hPC7   41  SCSWGPDDDGRTVDGPHQLGKAALQHGVIAGRQGFGSIFVVASGNGGEHN   90 rPC7  298  DNCNYDGYANSIYTVTIGAVDEEGRMPFYAEECASMLAVTFSGGDKMLRS  347
           |||||
hPC7   91  DNCNC.............................................   95
```

Fig. 5

MAMMALIAN PRO-HORMONE CONVERTASE

This application is a continuation-in-part of U.S. Ser. No. 08/510,347, filed Aug. 2, 1995, abandoned, and U.S. Ser. No. 08/517,015, filed Aug. 18, 1995, abandoned, both entitled Mammalian Pro-Hormone Convertase with inventors Nabil G. Seidah, Robert Day and Michel Chrétien. Both U.S. Ser. Nos. 08/510,347 and 08/517,015 are incorporated by reference as if set forth herein.

FIELD OF THE INVENTION

This invention relates to proteases, particularly to maturation enzymes, more particularly those of the subtilisin-kexin family.

BACKGROUND OF THE INVENTION

Numerous enzymes of the subtilisin-kexin family are known and they all have the characteristics of being able to recognize and cleave basic residues on proteic precursors. They differ from each other by their ability to cleave specific sequences containing mono- and dibasic residues. They also differ from each other by their tissue and intra-cellular distribution. In mammalians, pro-hormone convertases 1 to 6 are already known. A partial amino acid sequence of a new pro-hormone convertase has been obtained from a human squamous carcinoma cell line BEN. This amino acid sequence has been disclosed by an Australian group during a Keystone meeting that one of the inventors organized which was held at lake Tahoe, Calif. on March 2–8, 1995. This group presented a poster (Abstract number B7-102, J. Cellular Biochemistry, supplement 19B, 1995 p243), wherein it has been shown that a new maturation enzyme was co-expressed in BEN cells with parathyroid hormone-related protein. No nucleotide sequence has been disclosed.

STATEMENT OF THE INVENTION

It is an object of the present invention to provide a new enzyme that has been isolated from rat cells which shows a considerable degree of homology with the partial amino acid sequence of the above-identified human enzyme and which will be called heretofore rat pro-hormone convertase 7 (rPC7). This enzyme is a new member of the subtilisin-kexin family. This enzyme has an ubiquitous cell distribution, but which presence is particularly remarkable in immune system cells. The cDNA obtained from rat spleen has been partially sequenced and the amino acid sequence of rPC7 has been deduced therefrom. Furthermore, a cDNA encoding the partial amino acid sequence of the human PC7 has also been obtained, which sequence encodes a peptidic sequence identical to the one presented by the Australian group.

It is further an object of this invention to provide antibodies directed to PC7. These antibodies are useful to detect the presence or amount of PC7 in cells or tissues of different mammalian species, assuming a conservation of proteic sequence between species, if one relies on the similarity of sequences existing between rat and human PC7 partial proteic sequences. These antibodies are useful as diagnostic reagents to detect the presence and/or amount of PC7. Therefore a kit and a method for detecting the presence and/or amount of PC7 in cells or tissues are also aspects of this invention. Kits and methods are conceived for different purposes: Western blots, immunochemistry and immunological assays.

Nucleic acid probes and oligonucleotides and methods and kits for detecting PC7 nucleic acids, particularly messenger RNAs present in cells or tissues of different mammalian species are also an object of this invention. Methods and kits are developed in different forms: for polymerase chain reaction (PCR), in situ hybridization, Northern blots and detection of DNA fragments separated by electrophoresis, transferred and hybridized to labelled probes and oligonucleotides.

Diagnostic reagents and probes are useful in the detection of this novel enzyme. Negative or positive results will provide information to the user as to whether a proteic precursor of a protein of interest present in a cell will be cleaved or not, if this precursor bears basic residues recognizable by PC7. Such utility has been already demonstrated for other members of this family. For example, in corticotroph cell line AtT-20, the absence of PC2 has been correlated with the lack of production of alpha-MSH and beta-End. As another example, reactive hypoglycemia has been correlated with a deficiency in PC1 expression. Due to the specificity of cleavage of each pro-hormone convertase towards proteic precursors, this new enzyme may be useful in the maturation of precursors that have been found to be poor substrates to the already known convertases.

The nucleic acid sequence encoding PC7 and sub-fragments thereof constitute an insert that can be cloned in plasmidic vectors in a sense or anti-sense fashion. These vectors may be bacterial plasmids, phages and expression vectors. Recombinant expression vectors comprising a PC7 sense insert are usable to produce PC7 gene product. Recombinant expression vectors comprising a PC7 anti-sense insert are usable to silence the expression of PC7 gene.

Antisense oligonucleotides that are specific for PC7 are also usable to silence PC7 gene expression.

DESCRIPTION OF THE INVENTION

This invention will be described in details hereinbelow and by way of the appended figures, which purpose is to illustrate the invention rather than to limit its scope.

BRIEF DESCRIPTION OF THE FIGURES

FIGS. 1A and 1B represent Northern blot analyses of PC7 in rat, mouse and human cell lines (FIG. 1A) and across rat tissues (FIG. 1B). The estimated approximate size of PC7 mRNA is between 4.0–4.2 kb. The 22 established cell lines shown are [A] 12 constitutively secreting cells: HepG2 (hepatocellular carcinoma, human), Cos-1, (kidney, African green monkey), BSC40 (African green monkey kidney epithelial cells), BRL-3A (liver cells, Buffalo rat), Y1 (adrenal cortex, mouse), LoVo (colon adenocarcinoma, human), NIH/3T3 (embryo, mouse), Ltk⁻(connective tissue, mouse), TM3 (testicular Leydig cells, mouse), TM4 (testicular Sertoli cells, mouse), Caco-2 (colon adenocarcinoma, human) and LLC-PK$_1$ (proximal kidney tubule epithelial cells, pig). [B] 10 regulated cells containing endogenous secretory granules:. Neuro2A (neuroblastoma, mouse), NG-108 (neuroblastomaglioma hybrids, rat-mouse), SK-N-MIXC (neuroepithelioma, human), GH4Cl (somatomammotroph, rat), GH3 (somatomammotroph, rat), AtT-20 (corticotroph, mouse), αT3-1 (gonadotrophs, mouse), Rin m5F (insulinoma, rat), PC12 (pheochromocytoma, rat) and βTC-3 (insulinoma, mouse).

FIG. 3A–3C illustrate the partial cDNA and deduced amino acid sequences of rat PC7 (SEQ ID NOs: 6 and 5, respectively) (this sequence covers the entire structure of the active enzyme). FIG. 3A illustrates amino acid residues –36 to 269; FIG. 3B illustrates amino acid residues 270 to 617; FIG. 3C illustrate amino acid residues 618 to 747.

FIG. 4 shows alignment of partial nucleotidic sequences of rat (top) and human (bottom) PC7 (SEQ ID NO: 6 and SEQ ID NO: 4, respectively), wherein identical sequences are connected by a vertical line.

FIG. 5 shows alignment of partial amino acid sequences of human (top) and rat (bottom) active PC7 (SEQ ID NO: 5 (a.a. 198–347) and SEQ ID NO: 1, respectively), wherein sequences susceptible to be PC7 specific epitopes are underlined.

Figure 2A:
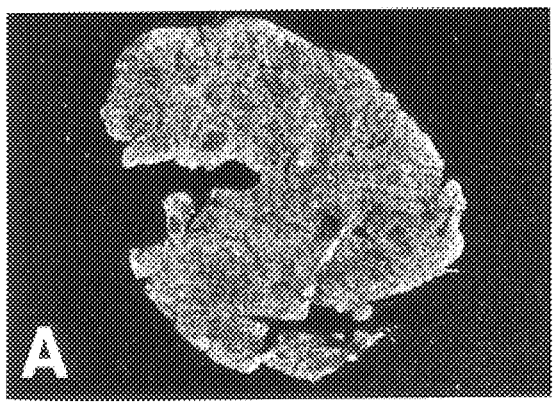
FIGS. 2a) to f) shows the results of in situ hybridization histochemistry demonstrating the mRNA distribution of PC7 in the rat (2A) thymus, (2C) spleen and (2E) lymph nodes. The specificity of the hybridization signal is demonstrated when compared to the adjacent controls shown in 2B, 2D and 2F, which were hybridized with the sense strand RNA probe. These data demonstrate that PC7 is expressed in various lymphocyte subpopulations including CD4+ and CD8+ cells. The CD4+cells are the targets of infection by the HIV retrovirus and hence the presence of PC7 may well be important for the activation of the surface glycoprotein gp160 needed for viral infectivity.

History of the discovery of PC7:

During a recent Keystone meeting that one of the inventors organized which was held at lake Tahoe, Calif. on March 2–8, 1995, an Australian group presented a poster (Abstract number B7-102, J. Cellular Biochemistry, supplement 19B, 1995 p243) in which they showed a deduced partial amino acid sequence of a novel subtilisin-kexin-like convertase based on a PCR fragment isolated from a human squamous carcinoma cell line BEN. No nucleotidic sequence was presented.

| Amino acid data presented by the Australian group |
| --- |
| His — Gly — Thr — Arg — Cys — Ala — Gly — Glu — Ser — Ala |
| Xxx — Ser — Ser — Pro — Asn — Asn — Ser — Phe — Cys — Ala |
| Val — Gly — Val — Ala — Tyr — Gly — Ser — Arg — Ile — Ala |
| Gly — Ile — Arg — Val — Leu — Asp — Gly — Pro — Leu — Thr |
| Asp — Ser — Met — Glu — Ala — Val — Ala — Phe — Asn — Lys |
| His — Tyr — Gln — Ile — Asn — Asp — Ile — Tyr — Ser — Cys |
| Ser — Trp — Gly — Pro — Asp — Asp — Asp — Gly — Lys — Thr |
| Val — Asp — Gly — Pro — His — Gln — Leu — Gly — Lys — Ala |
| Ala — Leu — Gln — His — Gly — Val — Ile — Ala — Gly — Arg |
| Gln — Gly — Phe — Glu — Gly — Ser — Ile — Phe — Val — Val |
| Ala — Ser — Gly — Asn — Gly — Gly — Glu — His — Asn — Asp |
| Asn — Cys — Asn — Cys     SEQ ID NO:1 |

Underlined amino acids represent the sequences which permitted the development of consensus degenerate sense and antisense oligonucleotides.

Strategy of the choice of degenerate oligonucleotides based on human protein sequence of PC7

Based on this amino acid sequence, degenerate oligonucleotides were developed, which allowed the inventors to isolate a cDNA encoding the same amino acid sequence from total RNA of BEN cells as well as the equivalent mRNA from rat pituitary mRNA.

|  |  | SEQ ID NO: |
| --- | --- | --- |
| Sense Oligonucleotide for hPCZ | | |
| hPC7 | Cys Ala Val Gly Val Ala Tyr Gly | 13 |
|  | TGT GCT GTG GGC GTG GCT TAC GGT | 14 |
|  |    C    C    C    T    C    C    T    C | 15 |
|  |             G    T       G    G    G         G | 16 |
|  |    A    A    A       A    A       A | 17 |
| Consensus | TGC GCC GTG GGC GTA GCA TAC GG | 18 |
|  |   T    T    A    T    C    T    T | 19 |
|  |                     G | 20 |
|  | TGY GCY GTR GGY GTV GCW TAY GG | 2 |
| hPACE4 | TGC ATC GTG GGC ATA GCG TAC AAT | 21 |
| mPACE4 | TGC ATC GTG GGC ATC GCA TAT AAT | 22 |
| rPACE4 | TGC ATC GTG GGC ATA GCA TAT AAT | 23 |
| hFurin | TGT GGT GTA GGT GTG GCC TAC AAC | 24 |
| mFurin | TGT GGC GTA GGT GTA GCT TAC AAT | 25 |
| rFurin | TGT GGT GTA GGT GTA GCT TAC AAT | 26 |
| mPC5 | TGC ACC GTC GGG ATC GCT TTC AAC | 27 |
| rPC5 | TGC ACC GTT GGA ATC GCT TTC AAC | 28 |
| mPC4 | TGT GGT GCC GGT GTG GCC TTC AAT | 29 |
| rPC4 | TGT GGT GCC GGT GTG GCC TTC AAT | 30 |
| mPC1 | TGT GGG GTT GGA GTT GCA TAT AAT | 31 |
| rPC1 | TGT GGA GTT GGA GTT GCA TAT AAT | 32 |
| hPC1 | TGC GGG GTT GGA GTT GCA TAC AAT | 33 |
| mPC2 | TGT GGA GTC GGC GTA GCA TAC AAC | 34 |
| rPC2 | TGT GGA GTC GGT GTA GCA TAC AAC | 35 |
| pPC2 | TGC GGG GTT GGA GTG GCC TAC AGC | 36 |
| hPC2 | TGT GGA GTT GGA GTA GCA TAC AAC | 37 |
| Antisense Oligonucleotide for hPC7 | | |
| hPC7 | Gly Gly Glu His Asn Asp Asn Cys Asn Cys | 38 |
|  | GGC GGC GAG CAC AAT GAT AAT TGT AAT TGT | 39 |
|  |  A    A    A      T    C      C      C    C      C | 40 |
|  |  T    T | |
|  |  G    G | |
| Consensus (Sense) | GGT GGC GAG CAC AAT GAC AAT TGT AAC TGT | 43 |
|  |  G    G    A    T    C         C      C         C | 44 |
|  | ACA GTT ACA ATT GTC ATT GTG CTC GCC ACC | 45 |

-continued

| | | SEQ ID NO: |
|---|---|---|
| (Antisense) | G G G G A T C C RCA GTT RCA RTT GTC RTT TTG YTC SCC MCC | 46 3 |
| hPACE4 | GGC GGG AGA GAG GGG GAC TAC TGC TCG TGC | 47 |
| mPACE4 | GGT GGG AGA GAA GGG GAC CAC TGC TCC TGT | 48 |
| rPACE4 | GGT GGG AGA GAA GGG GAC CAC TGC TCC TGT | 49 |
| hFurin | GGG GGC CGG GAA CAT GAC AGC TGC AAC TGC | 50 |
| mFurin | GGG GGC CGG GAA CAT GAC AGC TGC AAC TGT | 51 |
| rFurin | GGG GGC CGG GAA CAT GAC AGC TGT AAC TGT | 52 |
| mPC5 | GGT GGA CGG AGC AAG GAT CAC TGT TCT TGT | 53 |
| rPC5 | GGT GGA CGG AGT AAG GAC CAC TGC TCT TGT | 54 |
| mPC4 | GGT GGC CTC CAT TAC GAC AAC TGC AAT TGT | 55 |
| rPC4 | GGT GGC CTC CAC TAC GAC AAC TGC AAT TGT | 56 |
| mPC1 | GGG GGT CGT CAG GGA GAT AAC TGT GAC TGT | 57 |
| rPC1 | GGG GGT CGT CAA GGA GAT AAC TGT GAC TGT | 58 |
| hPC1 | GGG GGG CGT CAG GGA GAT AAT TGT GAC TGT | 59 |
| mPC2 | GGT GGC AGC TAC GAT GAC --- TGC AAC TGT | 60 |
| rPC2 | GGT GGC AGC TAC GAT GAC --- TGC AAC TGT | 61 |
| pPC2 | GGT GGC AGC TAC GAC GAC --- TGC AAC TGT | 62 |
| hPC2 | GGC GGC AGC TAT GAC GAC --- TGC AAC TGC | 63 |

Deduced nucleotide and amino acid sequences of rat and human PC7 derived from PCR clones Using reverse-transcriptase PCR on rat pituitary total RNA and oligo-dT, the inventors amplified first strand cDNAs. These were then primed with the sense and anti-sense consensus oligonucleotides in a typical PCR reaction of 30 cycles with 20 sec at 94° C., 1 min at 52° C. and 2 min at 72° C. The amplified cDNA of 285 nts was subcloned into the vector PCRII and several positive clones were sequenced by the automated ALF sequencer. One clone called R14 gave the rat PC7 sequence which was used for Northern blot analyses, in situ hybridization and to screen a lambda gt11 cDNA library from rat spleen. Two positive clones were isolated which permitted the identification of an extended rat cDNA sequence which encodes the complete protein. The active enzyme is encoded by amino acid residues 126 to 781 of SEQ ID NO: 5. The same strategy was used to isolate the cDNA sequence of human PC7 starting from RNA obtained from BEN cells. A fragment of 285 bp has been obtained and sequenced. A partial cDNA sequence of human PC7 is defined in SEQ ID NO: 4. The amino acid sequence deduced from SEQ ID NO: 4 is entirely comprised within the sequence disclosed by the Australian group.

Figure 2B:
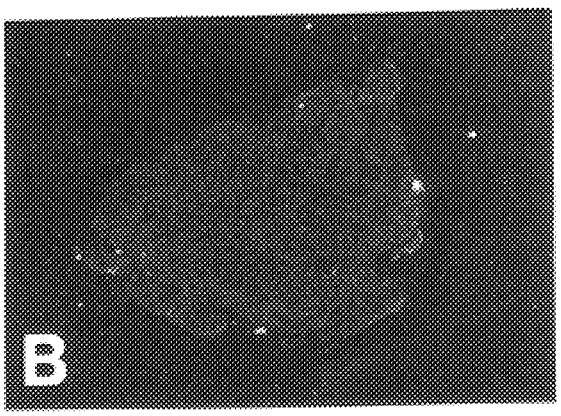
Figure 2C:
Figure 2D:
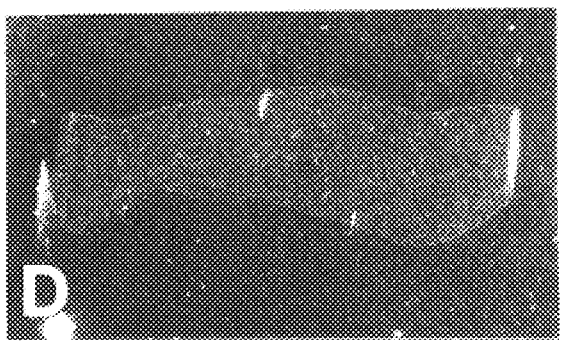
Figure 2E:
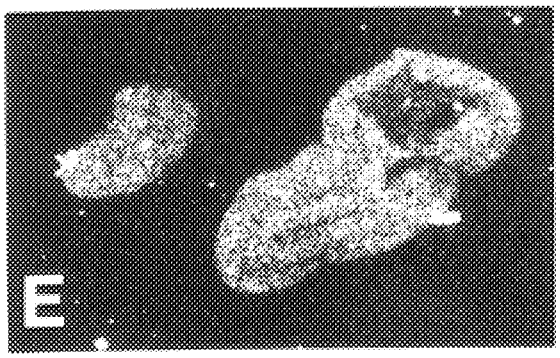
Figure 2F:
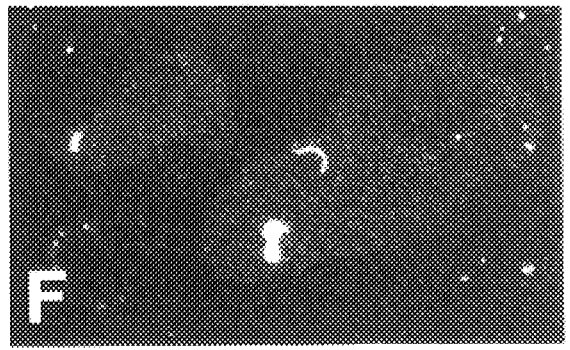

The rat 285 bp probe was then used to perform Northern blot of a multiplicity of cell lines as well as in situ hybridization studies in rat tissues and cells. Results on Northern blot are represented in FIG. 1 while those obtained from in situ hybridization are shown in FIG. 2. The data clearly show the following properties of this novel mRNA which was called PC7:

1) From Northern blot analyses, it appears that PC7 transcripts are ubiquitously expressed in all tissues and cells examined, suggesting a widespread distribution, similar to furin, as it is expressed in cells with constitutive and regulated secretory pathways.

2) The sum of the in situ and Northern data suggest that PC7 is most abundantly expressed in the colon, the spleen, the thymus and the lymph nodes, all of which are lymphoid-associated tissues.

3) Analysis of the cellular expression of PC7 in established cell lines confirmed the ubiquitous expression of PC7 in all cells but also demonstrated its conservation of sequence in various species such as mouse, rat, human and pig. The richest source of PC7 was the mouse pituitary alpha-T3-1 cell line derived from the gonadotrophs and the beta-TC3 cells line derived from a mouse insulinoma, the mouse fibroblast cell line Ltk⁻and the rat pheochromocytoma cell line PC12.

4) Furthermore, the expression of PC7 in the human colon carcinoma LoVo cell line is significant since this cell line is deficient in furin activity. This cell line is indeed known to express PACE4 and furin [Seidah, N. G., Chrétien, M. and Day, R. (1994) Biochimie 76, 197–209]. However, the LoVo furin has a point mutation which effectively makes it an inactive enzyme in this cell line [Takahashi, S., Kasai, K., Hatsuzawa, K., Kitamura, N., Misumi, Y., Ikehara, Y., Murakami, K. and Nakayama, K. (1993) Biochem. Biophys. Res. Commun. 195, 1019–1026.].

5) Evidence has been presented that an enzyme other than furin is capable of processing the HIV gp160 surface glycoprotein, based on [1] the ability of LoVo cells to activate this precursor into gp120/gp41 [Ohnishi, Y., Shioda, T., Nakayama, K., Iwata, S., Gotoh, B., Hamaguchi, M. and Nagai, Y. (1994) J. Virol. 68, 4075–4079], and [2] the results presented the inventors which demonstrated that in vitro gp160 is processed by both furin and PC1 into gp120/gp41 [Decroly, E., Vandenbranden, M., Ruysschaert, J. M., Cogniaux, J., Jacob, G. S., Howard, S. C., Marshall, G., Kompelli, A., Basak, A., Jean, F., Lazure, C., Benjannet, S., Chrétien, M., Day, R. and Seidah, N. G. (1994) J Biol Chem 269(16), 12240–12247]. However, in the inventors' laboratory, when gp160 was co-expressed in various cell lines with either PACE4, PC1, PC2, PC5 and its isoform PC5/6-B, furin was found to be by far the best processing enzyme of gp160. Yet, LoVo cells can efficiently process this precursor even though it is deficient in furin activity. This suggests that although furin is a good candidate processing enzyme of the AIDS virus gp160, another as yet undefined enzyme present in LoVo cells can also do the job. It is proposed that PC7 may well be the sought second candidate enzyme and not PACE4 which is a weak processor of gp160.

Deduced nucleotide and amino acid sequences of rat spleen PC7

Figure 3A:
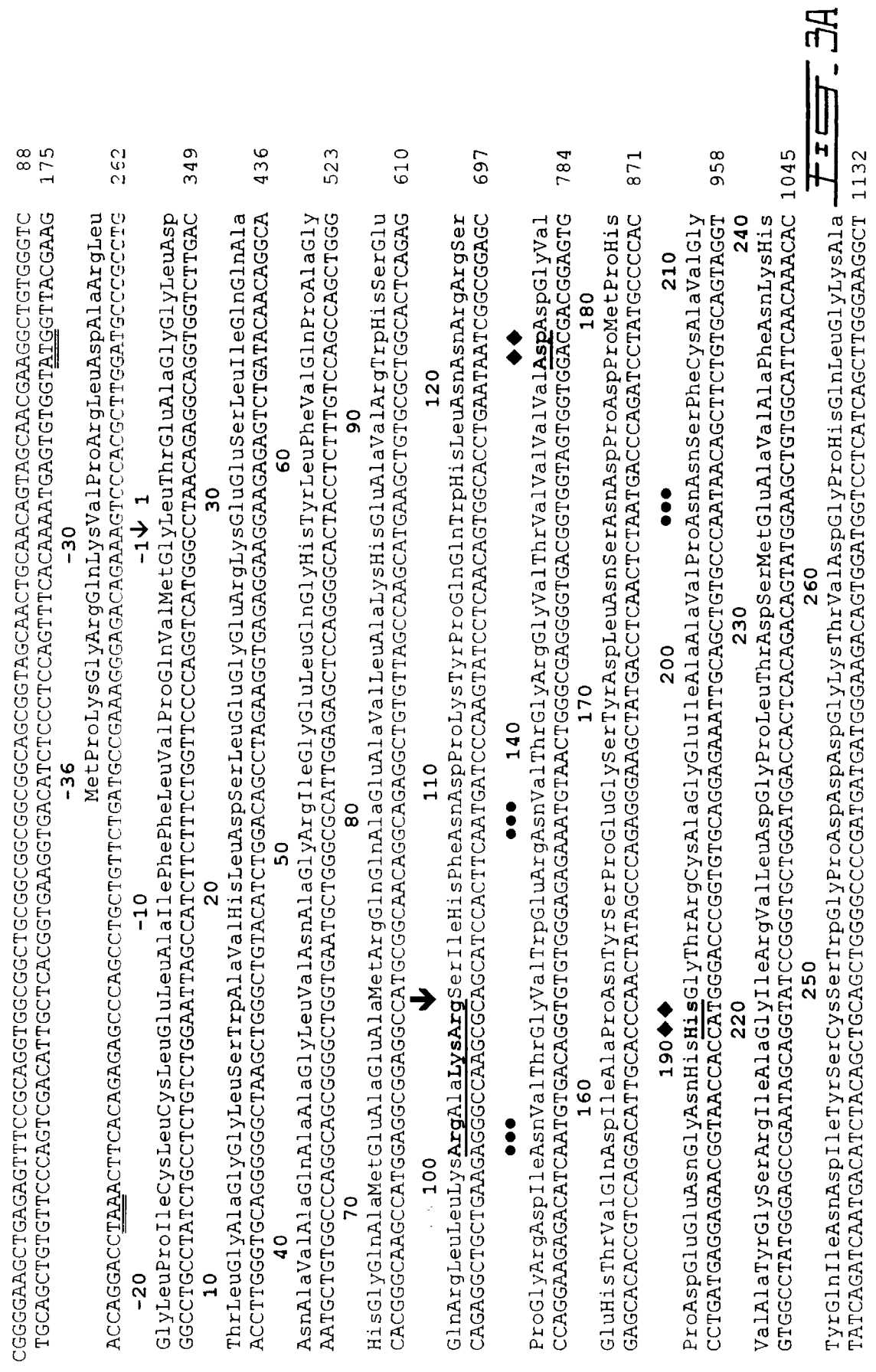

This sequence is shown in FIG. 3 and the amino acid and nucleotidic sequences are defined in SEQ ID. NO: 5 and 6, respectively. Referring to FIG. 3, the active sites $Asp^{150}$, His$^{191}$ and Ser$^{369}$ (bold, underlined), the oxyanion hole Asn$^{292}$ (bold) [♦♦], as well as the putative zymogen activation site ArgAlaLysArg [↓] are emphasized (SEQ ID NO: 65). The three putative Asn$^{130,138,204,474}$ glycosylation sites are also shown [●●●]. The other Asn$^{163}$ site is not acceptable for N-glycosylation in view of the Pro$^{166}$ residue. The predicted Ser, Thr phosphorylation [★★] and Tyr sulfatation [★] sites are depicted and the variant ArgArgGlySerLeu (amino acids 537–541 of SEQ ID NO: 5) sequence with its expected Ser phosphorylation site is also shown. Finally, the hydrophobic sequence, representing a putative transmembrane anchoring domain is underlined as: LeuValLeuValGlyCysPheSerValPheTrpThrIleTyrTyrMetLeu (SEQ ID NO: 64 The predicted polyadenylation signal AATAAA is also emphasized. The initiator methionine chosen occurs at nucleotide 218 giving a 36 amino acid signal peptide (–36 to –1). The presence of an in-phase ATG as well as the stop codon TAA is to be noted.

The available data will have important implications in pathologies of the immune system and in viral infections. These considerations were based on the following:
  a) The amino acid sequence of the catalytic domain of PC7 from both rat and human strongly suggest that PC7 will have a similar cleavage specificity to furin and would thus recognize both single basic residues and pairs of basic residues. Furthermore, based on the available specificity of furin [Siezen, R J, Creemers, J W M and Van de Ven, W J M. (1994) Eur. J. Biochem. 222, 255–266], it is suggested that PC7 may be better suited to cleave precursors with a negatively charged amino acid present three residues before the cleavage site (at P3) such as the case of the HIV gp160 where the cleavage site is Arg-Glu-Lys-Arg-↓ (SEQ ID NO: 66) and Glu occupies the P3 position.
  b) PC7 is ubiquitously distributed and its expression is particularly enriched in the immune system tissues and cells including the CD4+cells which are infectable by the HIV virus. PC7 is therefore a target of choice toward which future inhibitors may be developed to inhibit the conversion of HIV gp160 to gp120/gp41.
  c) The unique presence of an RRGSL sequence in the P-domain of PC7 which in all other members of the family is RRGDL is notable. This would imply a uniqueness of PC7 and may negate its possible interactions with surface integrin receptors which recognize the RGD sequence.

Alignment of the sequence of PC7 with the other members of the subtilisin-kexin family This alignment (not shown) demonstrates that PC7 represents an ancestral PC gene product as it best resembles the yeast kexin-like enzymes kex2, krp, kex1 and XRP-6 derived from four different yeast strains. In the mammalian PCs, the closest members are PC1 and PC2.

Nomenclature

This novel gene product is called PC7 since it represents the seventh member of the subtilisin-kexin family. It should be noted that the name PC7 was recently published to erroneously suggest that a reported rat sequence represents a seventh member of this family [Tsuji, AS. et al. Biochem Biophys. Res. Commun. 202, 1452–1459, 1994]. However, sequence alignment clearly demonstrated that the published rat PC7 sequence is nothing but rat PACE4 which also has been published [Johnson, R C et al. Endocrinology 135, 1178–1185, 1994]. Therefore, the present inventors have decided to keep the name PC7, as it accurately reflects the rank of this enzyme in order of discovery of the convertases.

Oligonucleotides useful as probes

Since nucleotidic sequences for rat and human PC7 have been obtained, it is now possible to deduce which are the conserved sequences that are usable to detect the presence and/or amount of PC7 in different species. Comparison of human and rat sequences are shown in FIG. 4. This alignment shows that a 38 nucleotide stretch (comprised between nucleotides 1043 and 1080 of SEQ ID NO: 6) is absolutely conserved between rat and human, suggesting that it could be used as an effective specific probe for the expression of PC7 in these species and presumably in other species. When this sequence was compared in both sense and anti sense orientations with the other six members of the mammalian family, the inventors calculated that the best alignment was with rat furin, PC4, PC2and PC5 at 63% identity. Therefore, it is believed that hybridization performed at high stringency will give a specific signal for PC7 in various mammalian species. The following oligonucleotides and part thereof that will give the same specific signal for PC7 in stringent conditions are 5'CAC TAT CAG ATC AAT GAC ATC TAC AGC TGC AGC TGG GG3', 5'CC CCA GCT GCA GCT GTA GAT GTC ATT GAT CTG ATA GTG3'(SEQ ID NO: 7 AND 8, respectively). They are to be used as well as the oligonucleotides which have the SEQ ID NOs: 2 and 3 and their reverse sequence (SEQ ID NOs: 11 and 12) as diagnosing reagents or as components of diagnostic kits to detect the presence and/or amount of PC7 encoding nucleic acids, preferably mRNAs, in conventional detection procedures (Northern blot, in situ hybridization, for example). A method of detection of PC7 which comprises the steps of contacting a cell sample (cells, tissues, lysates or cellular fractions thereof) with one the above oligonucleotides in selected hybridization conditions and detecting the presence and/or amount of hybridized oligonuleotides as an indication of the presence of PC7 is also new.

Development of specific antibodies to PC7

Alignment of peptidic sequences of rat and human PC7 is shown in FIG. 5. The sequence HisGlnLueGlyLysAlaAlaLeuGlnHis (SEQ ID NO: 9 corresponding to amino acid residues 265 to 274 of SEQ ID NO: 5) is absolutely conserved between the two species. It has only two amino acid identities with the other PCs (underlined). This peptidic sequence is therefore considered as a sequence of choice to raise antibodies specific to PC7. Another 17 amino acid sequence which is unique to rat PC7 is also assumed to be an antigen susceptible to entail of the production of specific antibodies to PC7: AlaSerTyrValSerProMetLeuLysGluAsnLysAlaValProArgSer (SEQ ID NO: 10 corresponding to amino acids 485 to 501 of SEQ ID NO: 5). This sequence is located in the C-terminal region which shows the greatest degree of divergence between PC7 and the other members of the family. It is assumed that this region will show a sufficient degree of similarity between species to entail of the production of antibodies recognizing PC7 in tissues or cells of different species. The antibodies raised against these peptides by using techniques well known in the art are to be used as diagnosing reagents or as components of diagnostic kits to detect the presence and/or amount of PC7 in conventional detection procedures (Western blot, immunohistochemistry, immunoassays, for example). A method of detection of PC7 which comprises the steps of contacting a cell sample (cells, tissues, lysates or cellular fractions thereof) with a specific anti-PC7 antibody in conditions allowing the binding of the antibodies to PC7 and detecting the presence and/or amount of bound antibodies as an indication of the presence of PC7 is also new.

Probing other mammalian PC7 enzymes

Part of totality of PC7 cDNA may be used to clone the same enzyme in other species, using either the cDNA as a probe to screen cDNA or genomic libraries or the PCR program outlined in this application. The oligonucleotides useful in the above diagnostic kit and method may be used as primers to initiate the PCR.

Recombinant plasmids and hosts

A variety of recombinant plasmids may now be constructed, using conventional techniques and commercially available plasmids. Expression vectors are particularly useful to produce PC7 in compatible host cells. It is also contemplated to insert the cDNA of PC7 in whole or in part in an antisense orientation in an expression vector such as pRcCMV or pcDNA-neo (InVitrogen) and to introduce these recombinant vectors in host cells by transfection or lipofection, for example, to silence the expression of PC7 gene in these cells. This procedure may be used in cell systems producing a proteic precursor wherein the presence of PC7 is undesirable, or to reveal pathologies correlated with a deficient production of PC7. Production of transgenic mice which are PC7deficient (silenced PC7) are particularly contemplated as "knock-out" animal models wherein associated pathologies will be revealed.

What is claimed is:

1. A pro-hormone convertase named PC7 isolated from rat tissue, having the amino acid sequence defined in SEQ ID NO: 5.

2. An isolated nucleic acid encoding the pro-hormone convertase of claim 1.

3. An isolated nucleic acid encoding a portion of the catalytic region of a human pro-hormone convertase corresponding to the rat pro-hormone convertase of claim 1, which has the nucleotidic sequence defined in SEQ ID NO: 4.

4. A peptidic fragment of the pro-hormone convertase defined in claim 1, which has the amino acid sequence defined in SEQ ID NO: 9 or 10.

5. A method of producing protein products from a proteic precursor, said proteic precursor comprising a sequence bearing basic amino acid residues which can be cleaved by PC7, comprising the steps of placing said precursor in the presence of the pro-hormone convertase of claim 1 and recovering said protein products.

6. An isolated nucleic acid as defined in claim 2 which has the nucleotidic sequence defined in SEQ ID NO: 6.

7. A recombinant DNA vector comprising the nucleic acid of claim 2.

8. A recombinant DNA vector comprising the nucleic acid of claim 3.

9. A method according to claim 5 wherein said proteic precursor is HIV gp160 glycoprotein and said protein products consist of HIV gp120 and gp41 glycoproteins.

10. A recombinant DNA vector comprising the nucleic acid of claim 6.

11. . A recombinant DNA vector according to claim 7 which is a recombinant mammalian expression vector.

12. A recombinant host cell comprising the recombinant DNA vector of claim 7.

13. A recombinant DNA vector according to claim 8 which is a recombinant mammalian expression vector.

14. A recombinant DNA vector according to claim 10 which is a recombinant mammalian expression vector.

15. A recombinant host cell comprising the recombinant DNA vector of claim 10.

16. A recombinant DNA vector according to claim 11 wherein said nucleic acid is inserted in an antisense orientation in said vector.

17. A recombinant host cell comprising the recombinant DNA vector of claim 11.

18. A recombinant DNA vector according to claim 13 wherein said nucleic acid is inserted in an antisense orientation in said vector.

19. A recombinant DNA vector according to claim 14 wherein said nucleic acid is inserted in an antisense orientation in said vector.

20. A recombinant host cell comprising the recombinant DNA of claim 14.

21. A method of producing PC7 comprising the steps of culturing the recombinant host cell of claim 17 and recovering PC7 from said cell or from the culture medium.

22. A method of producing PC7 comprising the steps of culturing the recombinant host cell of claim 21 and recovering PC7 from said cell or from the culture medium.

* * * * *

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
( A ) LENGTH: 114 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
His Gly Thr Arg Cys Ala Gly Glu Ser Ala Xaa Ser Ser Pro Asn Asn
1               5                   10                  15

Ser Phe Cys Ala Val Gly Val Ala Tyr Gly Ser Arg Ile Ala Gly Ile
            20                  25                  30

Arg Val Leu Asp Gly Pro Leu Thr Asp Ser Met Glu Ala Val Ala Phe
        35                  40                  45

Asn Lys His Tyr Gln Ile Asn Asp Ile Tyr Ser Cys Ser Trp Gly Pro
    50                  55                  60

Asp Asp Asp Gly Lys Thr Val Asp Gly Pro His Gln Leu Gly Lys Ala
65                  70                  75                  80

Ala Leu Gln His Gly Val Ile Ala Gly Arg Gln Gly Phe Glu Gly Ser
                85                  90                  95

Ile Phe Val Val Ala Ser Gly Asn Gly Gly Glu His Asn Asp Asn Cys
            100                 105                 110

Asn Cys
```

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Oligonucleotide"

( x i ) SEQUENCE DESCRIPTION: SEQ ID NO:2:

```
TGYGCYGTRG GYGTVGCWTA YGG                                          23
```

( 2 ) INFORMATION FOR SEQ ID NO:3:

( i ) SEQUENCE CHARACTERISTICS:
( A ) LENGTH: 30 base pairs
( B ) TYPE: nucleic acid (C) STRANDEDNESS: single
(D) TOPOLOGY: linear (i i) MOLECULE TYPE: other nucleic acid
(A) DESCRIPTION: /desc = "oligonucleotide"

(x i) SEQUENCE DESCRIPTION: SEQ ID NO:3:

RCAGTTRCAR TTGTCRTTRT GYTCSCCMCC                                                                30

(2) INFORMATION FOR SEQ ID NO:4:

(i) SEQUENCE CHARACTERISTICS:
(A) LENGTH: 285 base pairs
(B) TYPE: nucleic acid
(C) STRANDEDNESS: double
(D) TOPOLOGY: linear (i i) MOLECULE TYPE: cDNA (x i) SEQUENCE DESCRIPTION: SEQ ID NO:4:

| TGCGCTGTGG | GCGTAGCATA | TGGGAGCCGC | ATCGCAGGTA | TCCGGGTACT | GGATGGACCT | 60 |
| CTCACAGACA | GCATGGAGGC | GGTGGCGTTC | AACAAGCACT | ATCAGATCAA | TGACATCTAC | 120 |
| AGTTGCAGCT | GGGGACCAGA | TGACGATGGG | AGGACAGTGG | ATGGCCCCA | TCAGCTTGGA | 180 |
| AAGGCTGCCT | TACAACATGG | GGTGATTGCT | GGTCGCCAGG | GCTTTGGGAG | CATCTTTGTG | 240 |
| GTAGCCAGTG | GCAACGGTGG | GGAGCATAAC | GACAACTGTA | ACTGT | | 285 |

(2) INFORMATION FOR SEQ ID NO:5:

(i) SEQUENCE CHARACTERISTICS:
(A) LENGTH: 783 amino acids
(B) TYPE: amino acid
(C) STRANDEDNESS: single
(D) TOPOLOGY: linear (i i) MOLECULE TYPE: protein (x i) SEQUENCE DESCRIPTION: SEQ ID NO:5:

```
Met Pro Lys Gly Arg Gln Lys Val Pro Arg Leu Asp Ala Arg Leu Gly
  1               5                  10                  15

Leu Pro Ile Cys Leu Cys Leu Glu Leu Ala Ile Phe Phe Leu Val Pro
             20                  25                  30

Gln Val Met Gly Leu Thr Glu Ala Gly Gly Leu Asp Thr Leu Gly Ala
         35                  40                  45

Gly Gly Leu Ser Trp Ala Val His Leu Asp Ser Leu Glu Gly Glu Arg
     50                  55                  60

Lys Glu Glu Ser Leu Ile Gln Gln Ala Asn Ala Val Ala Gln Ala Ala
 65                  70                  75                  80

Gly Leu Val Asn Ala Gly Arg Ile Gly Glu Leu Gln Gly His Tyr Leu
                 85                  90                  95

Phe Val Gln Pro Ala Gly His Gly Gln Ala Met Glu Ala Glu Ala Met
            100                 105                 110

Arg Gln Gln Ala Glu Ala Val Leu Ala Lys His Glu Ala Val Arg Trp
        115                 120                 125

His Ser Glu Gln Arg Leu Leu Lys Arg Ala Lys Arg Ser Ile His Phe
    130                 135                 140

Asn Asp Pro Lys Tyr Pro Gln Gln Trp His Leu Asn Asn Arg Arg Ser
145                 150                 155                 160

Pro Gly Arg Asp Ile Asn Val Thr Gly Val Trp Glu Arg Asn Val Thr
                165                 170                 175

Gly Arg Gly Val Thr Val Val Val Val Asp Asp Gly Val Glu His Thr
```

-continued

|     |     |     |     |     | 180 |     |     |     | 185 |     |     |     | 190 |     |
|-----|-----|-----|-----|-----|-----|-----|-----|-----|-----|-----|-----|-----|-----|-----|
| Val | Gln | Asp | Ile | Ala | Pro | Asn | Tyr | Ser | Pro | Glu | Gly | Ser | Tyr | Asp | Leu |
|     |     |     | 195 |     |     |     | 200 |     |     |     | 205 |     |     |     |
| Asn | Ser | Asn | Asp | Pro | Asp | Pro | Met | Pro | His | Pro | Asp | Glu | Glu | Asn | Gly |
|     | 210 |     |     |     |     | 215 |     |     |     |     | 220 |     |     |     |
| Asn | His | His | Gly | Thr | Arg | Cys | Ala | Gly | Glu | Ile | Ala | Ala | Val | Pro | Asn |
| 225 |     |     |     |     | 230 |     |     |     |     | 235 |     |     |     |     | 240 |
| Asn | Ser | Phe | Cys | Ala | Val | Gly | Val | Ala | Tyr | Gly | Ser | Arg | Ile | Ala | Gly |
|     |     |     |     | 245 |     |     |     |     | 250 |     |     |     |     | 255 |     |
| Ile | Arg | Val | Leu | Asp | Gly | Pro | Leu | Thr | Asp | Ser | Met | Glu | Ala | Val | Ala |
|     |     |     |     | 260 |     |     |     |     | 265 |     |     |     |     | 270 |     |
| Phe | Asn | Lys | His | Tyr | Gln | Ile | Asn | Asp | Ile | Tyr | Ser | Cys | Ser | Trp | Gly |
|     |     |     | 275 |     |     |     |     | 280 |     |     |     |     | 285 |     |     |
| Pro | Asp | Asp | Asp | Gly | Lys | Thr | Val | Asp | Gly | Pro | His | Gln | Leu | Gly | Lys |
|     |     | 290 |     |     |     |     | 295 |     |     |     |     | 300 |     |     |     |
| Ala | Ala | Leu | Gln | His | Gly | Val | Met | Ala | Gly | Arg | Gln | Gly | Phe | Gly | Ser |
| 305 |     |     |     |     |     | 310 |     |     |     |     | 315 |     |     |     | 320 |
| Ile | Phe | Val | Val | Ala | Ser | Gly | Asn | Gly | Gly | Gln | His | Asn | Asp | Asn | Cys |
|     |     |     |     |     | 325 |     |     |     |     | 330 |     |     |     |     | 335 |
| Asn | Tyr | Asp | Gly | Tyr | Ala | Asn | Ser | Ile | Tyr | Thr | Val | Thr | Ile | Gly | Ala |
|     |     |     | 340 |     |     |     |     | 345 |     |     |     |     | 350 |     |     |
| Val | Asp | Glu | Glu | Gly | Arg | Met | Pro | Phe | Tyr | Ala | Glu | Glu | Cys | Ala | Ser |
|     |     | 355 |     |     |     |     | 360 |     |     |     |     | 365 |     |     |     |
| Met | Leu | Ala | Val | Thr | Phe | Ser | Gly | Gly | Asp | Lys | Met | Leu | Arg | Ser | Ile |
|     | 370 |     |     |     |     | 375 |     |     |     |     | 380 |     |     |     |     |
| Val | Thr | Thr | Asp | Trp | Asp | Leu | Gln | Lys | Gly | Thr | Gly | Cys | Thr | Glu | Gly |
| 385 |     |     |     |     | 390 |     |     |     |     | 395 |     |     |     |     | 400 |
| His | Thr | Gly | Thr | Ser | Ala | Ala | Ala | Pro | Leu | Ala | Ala | Gly | Met | Ile | Ala |
|     |     |     |     | 405 |     |     |     |     | 410 |     |     |     |     | 415 |     |
| Leu | Met | Leu | Gln | Val | Arg | Pro | Cys | Leu | Thr | Trp | Arg | Asp | Val | Gln | His |
|     |     |     |     | 420 |     |     |     |     | 425 |     |     |     |     | 430 |     |
| Ile | Ile | Val | Phe | Thr | Ala | Thr | Gln | Tyr | Glu | Asp | His | Arg | Ala | Asp | Trp |
|     |     |     | 435 |     |     |     |     | 440 |     |     |     |     | 445 |     |     |
| Leu | Thr | Asn | Glu | Ala | Gly | Phe | Ser | His | Ser | His | Gln | His | Gly | Phe | Gly |
|     |     | 450 |     |     |     |     | 455 |     |     |     |     | 460 |     |     |     |
| Leu | Leu | Asn | Ala | Trp | Arg | Leu | Val | Asn | Ala | Ala | Lys | Ile | Trp | Thr | Ser |
| 465 |     |     |     |     | 470 |     |     |     |     | 475 |     |     |     |     | 480 |
| Val | Pro | Tyr | Leu | Ala | Ser | Tyr | Val | Ser | Pro | Met | Leu | Lys | Glu | Asn | Lys |
|     |     |     |     | 485 |     |     |     |     | 490 |     |     |     |     | 495 |     |
| Ala | Val | Pro | Arg | Ser | Pro | His | Ser | Leu | Glu | Val | Leu | Trp | Asn | Val | Ser |
|     |     |     | 500 |     |     |     |     | 505 |     |     |     |     | 510 |     |     |
| Arg | Thr | Asp | Leu | Glu | Met | Ser | Gly | Leu | Lys | Thr | Leu | Glu | His | Val | Ala |
|     |     | 515 |     |     |     |     | 520 |     |     |     |     | 525 |     |     |     |
| Val | Thr | Val | Ser | Ile | Thr | His | Pro | Arg | Arg | Gly | Ser | Leu | Glu | Leu | Lys |
|     | 530 |     |     |     |     | 535 |     |     |     |     | 540 |     |     |     |     |
| Leu | Phe | Cys | Pro | Ser | Gly | Met | Met | Ser | Leu | Ile | Gly | Ala | Pro | Arg | Ser |
| 545 |     |     |     |     | 550 |     |     |     |     | 555 |     |     |     |     | 560 |
| Met | Asp | Ser | Asp | Pro | Asn | Gly | Phe | Asn | Asp | Trp | Thr | Phe | Ser | Thr | Val |
|     |     |     |     | 565 |     |     |     |     | 570 |     |     |     |     | 575 |     |
| Arg | Cys | Trp | Gly | Glu | Arg | Ala | Arg | Gly | Val | Tyr | Arg | Leu | Val | Ile | Arg |
|     |     |     |     | 580 |     |     |     |     | 585 |     |     |     |     | 590 |     |
| Asp | Val | Gly | Asp | Glu | Pro | Leu | Gln | Val | Gly | Ile | Leu | Gln | Gln | Trp | Gln |
|     |     | 595 |     |     |     |     | 600 |     |     |     |     | 605 |     |     |     |

|     |     |     |     |     |     |     |     |     |     |     |     |     |     |     |
| --- | --- | --- | --- | --- | --- | --- | --- | --- | --- | --- | --- | --- | --- | --- |
| Leu | Thr 610 | Leu | Tyr | Gly | Ser | Thr 615 | Trp | Ser | Pro | Val | Asp 620 | Ile | Lys | Asp | Arg |
| Gln 625 | Ser | Leu | Leu | Glu | Ser 630 | Ala | Met | Ser | Gly | Lys 635 | Tyr | Leu | His | Asp | Asp 640 |
| Phe | Thr | Leu | Pro | Cys 645 | Pro | Pro | Gly | Leu | Lys 650 | Ile | Pro | Glu | Glu | Asp 655 | Gly |
| Tyr | Ser | Ile | Thr 660 | Pro | Asn | Thr | Leu | Lys 665 | Thr | Leu | Val | Leu 670 | Gly | Cys |
| Phe | Ser | Val 675 | Phe | Trp | Thr | Ile | Tyr 680 | Tyr | Met | Leu | Glu | Val 685 | Cys | Leu | Ser |
| Gln | Arg 690 | Ser | Lys | Ala | Ser | Thr 695 | His | Gly | Cys | Arg | Arg 700 | Gly | Cys | Cys | Pro |
| Trp 705 | Pro | Pro | Gln | Ser | Gln 710 | Asn | Ser | Lys | Glu | Val 715 | Gly | Thr | Ala | Leu | Glu 720 |
| Ser | Met | Pro | Leu | Cys 725 | Ser | Ser | Lys | Asp | Leu 730 | Asp | Gly | Val | Asp | Ser 735 | Glu |
| His | Gly | Asp | Cys 740 | Thr | Thr | Ala | Ser | Ser 745 | Leu | Leu | Ala | Pro | Glu 750 | Leu | Leu |
| Gly | Glu | Ala 755 | Asp | Trp | Ser | Leu | Ser 760 | Gln | Asn | Ser | Lys | Ser 765 | Asp | Leu | Asp |
| Cys | Pro 770 | Pro | His | Gln | Pro 775 | Pro | Asp | Leu | Lys | Asp 780 | Gly | Gln | Ile | Cys |

( 2 ) INFORMATION FOR SEQ ID NO:6:

( i ) SEQUENCE CHARACTERISTICS:
        ( A ) LENGTH: 3450 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

```
CGGGGAAGCT  GAGAGTTTCC  GCAGGTGGCG  GCTGCGGCGG  CGGCGGCAGC  GGTAGCAACT      60
GCAACAGTAG  CAACGAAGGC  TGTGGGTCTG  CAGCTGTGTT  CCCAGTCGAC  ATTGCTCACG     120
GTGAAGGTGA  CATCTCCCTC  CAGTTTCACA  AAATGAGTGT  GGTATGGTTA  CGAAGACCAG     180
GACCTAAACT  TCACAGAGAG  CCCAGCCTGC  TGTTCTGATG  CCGAAAGGGA  GACAGAAAGT     240
CCCACGCTTG  GATGCCCGCC  TGGGCCTGCC  TATCTGCCTC  TGTCTGGAAT  TAGCCATCTT     300
CTTTCTGGTT  CCCCAGGTCA  TGGGCCTAAC  AGAGGCAGGT  GGTCTTGACA  CCTTGGGTGC     360
AGGGGGGCTA  AGCTGGGCTG  TACATCTGGA  CAGCCTAGAA  GGTGAGAGGA  AGGAAGAGAG     420
TCTGATACAA  CAGGCAAATG  CTGTGGCCCA  GGCAGCGGGG  CTGGTGAATG  CTGGGCGCAT     480
TGGAGAGCTC  CAGGGGCACT  ACCTCTTTGT  CCAGCCAGCT  GGGCACGGGC  AAGCCATGGA     540
GGCGGAGGCC  ATGCGGCAAC  AGGCAGAGGC  TGTGTTAGCC  AAGCATGAAG  CTGTGCGCTG     600
GCACTCAGAG  CAGAGGCTGC  TGAAGAGGGC  CAAGCGCAGC  ATCCACTTCA  TGATCCCAA      660
GTATCCTCAA  CAGTGGCACC  TGAATAATCG  GCGGAGCCCA  GGAAGAGACA  TCAATGTGAC     720
AGGTGTGTGG  GAGAGAAATG  TAACTGGGCG  AGGGGTGACG  GTGGTAGTGG  TGGACGACGG     780
AGTGGAGCAC  ACCGTCCAGG  ACATTGCACC  CAACTATAGC  CCAGAGGGAA  GCTATGACCT     840
CAACTCTAAT  GACCCAGATC  CTATGCCCCA  CCCTGATGAG  GAGAACGGTA  ACCACCATGG     900
GACCCGGTGT  GCAGGAGAAA  TTGCAGCTGT  GCCCAACAAC  AGCTTCTGTG  CAGTAGGTGT     960
GGCCTATGGG  AGCCGAATAG  CAGGTATCCG  GGTGCTGGAT  GGACCACTCA  CAGACAGTAT    1020
```

| | | | | | | |
|---|---|---|---|---|---|---|
| GGAAGCTGTG | GCATTCAACA | AACACTATCA | GATCAATGAC | ATCTACAGCT | GCAGCTGGGG | 1080 |
| CCCCGATGAT | GATGGGAAGA | CAGTGGATGG | TCCTCATCAG | CTTGGGAAGG | CTGCCTTACA | 1140 |
| ACATGGAGTG | ATGGCTGGTC | GCCAAGGCTT | TGGAAGTATC | TTTGTGGTTG | CCAGTGGTAA | 1200 |
| TGGTGGCCAG | CACAATGACA | ACTGCAACTA | TGATGGCTAT | GCCAACTCCA | TCTACACTGT | 1260 |
| CACCATAGGA | GCTGTGGATG | AGGAGGGACG | GATGCCTTTT | TATGCAGAGG | AGTGTGCCTC | 1320 |
| CATGCTGGCA | GTCACCTTCA | GTGGAGGAGA | CAAGATGCTG | CGGAGCATTG | TGACTACTGA | 1380 |
| CTGGGACCTT | CAGAAGGGCA | CTGGCTGCAC | TGAAGGCCAC | ACAGGAACCT | CAGCTGCAGC | 1440 |
| CCCTCTAGCA | GCTGGCATGA | TAGCTCTCAT | GCTGCAGGTG | CGGCCCTGCC | TCACGTGGCG | 1500 |
| GGATGTCCAG | CACATCATTG | TCTTCACAGC | CACTCAGTAT | GAAGATCATC | GTGCAGACTG | 1560 |
| GCTCACTAAT | GAGGCTGGAT | TCAGCCACAG | CCATCAGCAT | GGTTTCGGCC | TGCTCAACGC | 1620 |
| CTGGAGACTT | GTCAATGCAG | CCAAGATCTG | GACGTCTGTC | CCTTACTTAG | CTTCCTATGT | 1680 |
| CAGCCCCATG | CTGAAAGAAA | ATAAGGCTGT | TCCACGGTCC | CCCCACTCTC | TGGAGGTCCT | 1740 |
| ATGGAATGTC | AGCAGGACGG | ACCTGGAGAT | GTCGGGGCTG | AAGACCCTGG | AACATGTGGC | 1800 |
| GGTGACAGTC | TCCATCACTC | ACCCACGACG | TGGCAGCTTA | GAACTGAAAC | TGTTTTGTCC | 1860 |
| CAGTGGCATG | ATGTCTTTGA | TCGGCGCGCC | CCGCAGCATG | GACTCGGACC | CTAACGGCTT | 1920 |
| CAATGACTGG | ACATTTTCCA | CTGTGCGGTG | CTGGGGGAA | AGAGCAAGAG | GAGTCTACAG | 1980 |
| ACTGGTTATC | AGGGATGTAG | GAGATGAGCC | GCTCCAGGTG | GGCATCCTCC | AGCAGTGGCA | 2040 |
| GCTGACGCTG | TATGGCTCCA | CGTGGAGTCC | AGTAGACATC | AAGGACAGAC | AAAGTCTCTT | 2100 |
| AGAAAGTGCT | ATGAGTGGAA | AATACCTGCA | TGATGACTTC | ACTCTGCCTT | GCCCACCTGG | 2160 |
| ACTGAAAATT | CCTGAGGAGG | ATGGTTACAG | CATTACCCCT | AACACACTCA | AGACCCTTGT | 2220 |
| GCTGGTTGGC | TGCTTCAGTG | TCTTCTGGAC | CATTTACTAC | ATGCTAGAAG | TGTGCCTGAG | 2280 |
| CCAGAGGAGC | AAGGCTTCCA | CCCATGGCTG | CAGGAGAGGA | TGCTGCCCCT | GGCCCCACA | 2340 |
| AAGCCAAAAC | TCCAAGGAAG | TGGGACAGC | ACTAGAATCA | ATGCCACTGT | GCAGCAGCAA | 2400 |
| GGACCTGGAT | GGAGTGGATT | CAGAGCACGG | GGACTGCACA | ACTGCCTCTA | GCTTGCTGGC | 2460 |
| CCCAGAGCTG | CTGGGGGAAG | CTGACTGGAG | TCTGTCCCAG | AACAGTAAGA | GTGACCTGGA | 2520 |
| TTGTCCTCCC | CACCAACCCC | CAGACCTGAA | GGATGGACAG | ATCTGCTGAC | CCCAGAGCCC | 2580 |
| AGCTTCTTCC | ATGTACAACA | GGCTCTTCCT | AAACTTGGTT | ATGAGGCTTT | CAATCATGGA | 2640 |
| TGCTCAGGAG | AGAATGGTCC | TGATAGTGAC | ATCTGCCACC | CAAGGCCTCT | GAAGCATTCT | 2700 |
| CAGCCTTCTC | AAGAGGGTGA | GGGCCATCTT | AATTAAGCGC | AGTGGTAAGG | GACTGGTGTT | 2760 |
| CATGGCTCCT | CTAGCTGAGC | TTTGCTGAGA | GCCTTTCGAC | AAGGGGTTGG | CGCCCAGGCC | 2820 |
| AGGCAGCCCT | TGATTTCATC | TCTCTCGGGC | TAGTCACTGT | CCTCGGCCAT | CAGGACCTCC | 2880 |
| ACCCCTTCAC | AAGTTATGCA | GCAGGTGCCT | GTATACCTAG | GAACACTCTC | AACAGAAGTG | 2940 |
| CCGCTGTACC | GAGGGCCCAG | AGAGAGGCTG | GCAAGAGCCT | AGACATGCCT | ACCCTGAAAG | 3000 |
| CAGCTGCCTT | CATTACCCTT | TCCTGTGTGC | CTGTTCTGAA | GCCCGTACCT | TCACTACCAC | 3060 |
| TCACCCTTCC | TGCTGAAGGA | ATGGTGGCGT | GTCCCAGGAA | AACTGGGAGG | CACAGGATTC | 3120 |
| CCAGCCAGCA | CCCTTGCTGC | CTCACTGGGG | AAGTTGGCCT | GCTGGGCTGC | AGAGAGCTGA | 3180 |
| GACACAGTGT | TGTCTAAGAT | AGCATGGGAG | CCCCTGCCTA | TGACCACCTG | TCTTCCTCTG | 3240 |
| CAAAGTGCTC | AGGGAAATGG | CCTTCATTCC | AGAGGCCAGC | TGTCCGCCTG | ACTTTTCCTC | 3300 |
| CATTCTTGGC | CTTCTCCCCT | TCCCATCTTT | GGAGCTAATT | GTTAATATGA | ATTTTTTAAT | 3360 |
| GCTTAAGATT | TGATTTTTAC | TTTTCAAAGC | AACATTTTGT | TGAATTTTTT | TCTGCACAGC | 3420 |

| | |
|---|---:|
| TTTCCAAAAT AAAAAGCAGA AGTAAAAAAA | 3450 |

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:7:

| | |
|---|---:|
| CACTATCAGA TCAATGACAT CTACAGCTGC AGCTGGGG | 38 |

( 2 ) INFORMATION FOR SEQ ID NO:8:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:8:

| | |
|---|---:|
| CCCCAGCTGC AGCTGTAGAT GTCATTGATC TGATAGTG | 38 |

( 2 ) INFORMATION FOR SEQ ID NO:9:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
His  Gln  Leu  Gly  Lys  Ala  Ala  Leu  Gln  His
1              5                             10
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Ala  Ser  Tyr  Val  Ser  Pro  Met  Leu  Lys  Glu  Asn  Lys  Ala  Val  Pro  Arg
1              5                        10                            15

Ser
```

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:11:

CCRTAWGCBA CRCCYACRGC RCA 23

( 2 ) INFORMATION FOR SEQ ID NO:12:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:12:

GGKGGSGARC AYAAYGACAA YTGYAACTGY 30

( 2 ) INFORMATION FOR SEQ ID NO:13:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

Cys Ala Val Gly Val Ala Tyr Gly
1               5

( 2 ) INFORMATION FOR SEQ ID NO:14:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:14:

TGTGCTGTGG GCGTGGCTTA CGGT 24

( 2 ) INFORMATION FOR SEQ ID NO:15:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:15:

TGCGCCGTCG GTGTCGCCTA TGGC 24

( 2 ) INFORMATION FOR SEQ ID NO:16:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

(x i) SEQUENCE DESCRIPTION: SEQ ID NO:16:

TGTGCGGTTG GGGTGGCGTA CGGG  24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "oligonucleotide"

(x i) SEQUENCE DESCRIPTION: SEQ ID NO:17:

TGTGCAGTAG GAGTAGCATA CGGA  24

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "oligonucleotide"

(x i) SEQUENCE DESCRIPTION: SEQ ID NO:18:

TGCGCCGTGG GCGTAGCATA CGG  23

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "oligonucleotide"

(x i) SEQUENCE DESCRIPTION: SEQ ID NO:19:

TGTGCTGTAG GTGTCGCTTA TGG  23

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "oligonucleotide"

(x i) SEQUENCE DESCRIPTION: SEQ ID NO:20:

TGCGCCGTGG GCGTGGCATA CGG  23

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "oligonucleotide"

( x i ) SEQUENCE DESCRIPTION: SEQ ID NO:21:

TGCATCGTGG GCATAGCGTA CAAT  24

( 2 ) INFORMATION FOR SEQ ID NO:22:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:22:

TGCATCGTGG GCATCGCATA TAAT  24

( 2 ) INFORMATION FOR SEQ ID NO:23:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:23:

TGCATCGTGG GCATAGCATA TAAT  24

( 2 ) INFORMATION FOR SEQ ID NO:24:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:24:

TGTGGTGTAG GTGTGGCCTA CAAC  24

( 2 ) INFORMATION FOR SEQ ID NO:25:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

( x i ) SEQUENCE DESCRIPTION: SEQ ID NO:25:

TGTGGCGTAG GTGTAGCTTA CAAT  24

( 2 ) INFORMATION FOR SEQ ID NO:26:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "oligonucleotide"

-continued (xi) SEQUENCE DESCRIPTION: SEQ ID NO:26:

TGTGGTGTAG GTGTAGCTTA CAAT 24

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:27:

TGCACCGTCG GGATCGCTTT CAAC 24

(2) INFORMATION FOR SEQ ID NO:28:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:28:

TGCACCGTTG GAATCGCTTT CAAC 24

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:29:

TGTGGTGCCG GTGTGGCCTT CAAT 24

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:30:

TGTGGTGCCG GTGTGGCCTT CAAT 24

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

( x i ) SEQUENCE DESCRIPTION: SEQ ID NO:31:

TGTGGGGTTG GAGTTGCATA TAAT                                    24

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:32:

TGTGGAGTTG GAGTTGCATA TAAT                                    24

( 2 ) INFORMATION FOR SEQ ID NO:33:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:33:

TGCGGGGTTG GAGTTGCATA CAAT                                    24

( 2 ) INFORMATION FOR SEQ ID NO:34:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:34:

TGTGGAGTCG GCGTAGCATA CAAC                                    24

( 2 ) INFORMATION FOR SEQ ID NO:35:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:35:

TGTGGAGTCG GTGTAGCATA CAAC                                    24

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:36:

TGCGGGGTTG GAGTGGCCTA CAGC 24

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:37:

TGTGGAGTTG GAGTAGCATA CAAC 24

( 2 ) INFORMATION FOR SEQ ID NO:38:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

Gly Gly Glu His Asn Asp Asn Cys Asn Cys
1               5                   10

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:39:

GGCGGCGAGC ACAATGATAA TTGTAATTGT 30

( 2 ) INFORMATION FOR SEQ ID NO:40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:40:

GGAGGAGAAC ATAACGACAA CTGCAACTGC 30

( 2 ) INFORMATION FOR SEQ ID NO:41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

(xi) SEQUENCE DESCRIPTION: SEQ ID NO:41:

GGTGGTGAGC ACAATGATAA TTGTAATTGT                30

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:42:

GGGGGGGAGC ACAATGATAA TTGTAATTGT                30

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:43:

GGTGGCGAGC ACAATGACAA TTGTAACTGT                30

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:44:

GGGGGGGAAC ATAACGACAA CTGCAACTGC                30

(2) INFORMATION FOR SEQ ID NO:45:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:45:

ACAGTTACAA TTGTCATTGT GCTCGCCACC                30

(2) INFORMATION FOR SEQ ID NO:46:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

( x i ) SEQUENCE DESCRIPTION: SEQ ID NO:46:

GCAGTTGCAG TTGTCGTTAT GTTCCCCCCC  30

( 2 ) INFORMATION FOR SEQ ID NO:47:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:47:

GGCGGGAGAG AGGGGACTA CTGCTCGTGC  30

( 2 ) INFORMATION FOR SEQ ID NO:48:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:48:

GGTGGGAGAG AAGGGGACCA CTGCTCCTGT  30

( 2 ) INFORMATION FOR SEQ ID NO:49:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:49:

GGTGGGAGAG AAGGGGACCA CTGCTCCTGT  30

( 2 ) INFORMATION FOR SEQ ID NO:50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:50:

GGGGGCCGGG AACATGACAG CTGCAACTGC  30

( 2 ) INFORMATION FOR SEQ ID NO:51:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:51:

GGGGGCCGGG AACATGACAG CTGCAACTGT 30

( 2 ) INFORMATION FOR SEQ ID NO:52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:52:

GGGGGCCGGG AACATGACAG CTGTAACTGT 30

( 2 ) INFORMATION FOR SEQ ID NO:53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:53:

GGTGGACGGA GCAAGGATCA CTGTTCTTGT 30

( 2 ) INFORMATION FOR SEQ ID NO:54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:54:

GGTGGACGGA GTAAGGACCA CTGCTCTTGT 30

( 2 ) INFORMATION FOR SEQ ID NO:55:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:55:

GGTGGCCTCC ATTACGACAA CTGCAATTGT 30

( 2 ) INFORMATION FOR SEQ ID NO:56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:56:

GGTGGCCTCC ACTACGACAA CTGCAATTGT 30

( 2 ) INFORMATION FOR SEQ ID NO:57:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:57:

GGGGGTCGTC AGGGAGATAA CTGTGACTGT 30

( 2 ) INFORMATION FOR SEQ ID NO:58:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:58:

GGGGGTCGTC AAGGAGATAA CTGTGACTGT 30

( 2 ) INFORMATION FOR SEQ ID NO:59:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:59:

GGGGGGCGTC AGGGAGATAA TTGTGACTGT 30

( 2 ) INFORMATION FOR SEQ ID NO:60:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:60:

GGTGGCAGCT ACGATGACTG CAACTGT 27

( 2 ) INFORMATION FOR SEQ ID NO:61:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:61:

GGTGGCAGCT ACGATGACTG CAACTGT    27

( 2 ) INFORMATION FOR SEQ ID NO:62:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:62:

GGTGGCAGCT ACGACGACTG CAACTGT    27

( 2 ) INFORMATION FOR SEQ ID NO:63:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:63:

GGCGGCAGCT ATGACGACTG CAACTGC    27

( 2 ) INFORMATION FOR SEQ ID NO:64:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:64:

Leu Val Leu Val Gly Cys Phe Ser Val Phe Trp Thr Ile Tyr Tyr Met
1               5                   10                  15

Leu ( 2 ) INFORMATION FOR SEQ ID NO:65:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:65:

Arg Ala Lys Arg
1

( 2 ) INFORMATION FOR SEQ ID NO:66:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide (x i) SEQUENCE DESCRIPTION: SEQ ID NO:66:

Arg Glu Lys Arg
1